United States Patent [19]

Smith

[11] 3,959,369

[45] May 25, 1976

[54] ALKANOLAMINE DERIVATIVES
[75] Inventor: Leslie Harold Smith, Macclesfield, England
[73] Assignee: Imperial Chemical Industries Limited, London, England
[22] Filed: Nov. 25, 1974
[21] Appl. No.: 526,921

[30] Foreign Application Priority Data
Dec. 12, 1973  United Kingdom............ 57517/73

[52] U.S. Cl.................. 260/553 R; 260/553 A; 260/558 A; 260/559 S; 260/559 A; 260/559 B; 424/321
[51] Int. Cl.²............................ C07C 103/30
[58] Field of Search......... 260/553 A, 553 R, 559 S, 260/559 A, 559 B

[56] References Cited
UNITED STATES PATENTS

| | | | |
|---|---|---|---|
| 3,676,493 | 7/1972 | Smith................... | 260/559 A |
| 3,726,919 | 4/1973 | Wooldridge et al........... | 260/553 R |
| 3,845,123 | 10/1974 | Cox et al................ | 260/553 A |
| 3,888,898 | 6/1975 | Koppe et al............... | 260/553 R |

Primary Examiner—C. Davis
Attorney, Agent, or Firm—Cushman, Darby & Cushman

[57] ABSTRACT

Novel 1-amidoaryloxy-3-amidoalkylamino-2-propanol derivatives, processes for their manufacture, pharmaceutical compositions containing them and methods of using them in the treatment of heart diseases. The compounds possess β-adrenergic blocking activity. Representative of the compounds disclosed is 1-o-(N-β-hydroxyethylcarbamoylmethoxy)-phenoxy-3-β-isobutyramidoethylamino-2-propanol.

12 Claims, No Drawings

ALKANOLAMINE DERIVATIVES

This invention relates to new alkanolamine derivatives which possess β-adrenergic blocking activity. The invention is a modification of that claimed in U.K. Application No. 57970/72.

According to the invention there is provided a new alkanolamine derivative of the formula:

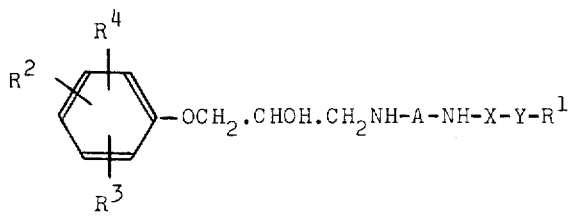

wherein A stands for an alkylene radical of from 2 to 12 carbon atoms; wherein $R^1$ stands for the hydrogen atom or for an alkyl, halogenoalkyl, alkenyl or cycloalkyl radical each of up to 10 carbon atoms, or for an aryl radical of the formula:

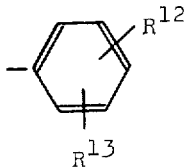

wherein $R^2$, $R^3$, $R^{12}$ and $R^{13}$, which may be the same or different, each stands for a hydrogen or halogen atom, a hydroxy, amino, nitro or cyano radical, an alkyl, cycloalkyl, alkenyl, alkynyl, alkoxy, alkylthio, cycloalkoxy, alkenyloxy, alkynyloxy or alkanoyl radical each of up to 6 carbon atoms, or an aryl, aryloxy or aralkoxy radical each of up to 12 carbon atoms; or wherein $R^{12}$ and $R^{13}$ together form the trimethylene, tetramethylene, 1-oxotetramethylene, propenylene, but-2-enylene or buta-1,3-dienylene radical such that together with the adjacent benzene ring they form respectively the indanyl, 5,6,7,8-tetrahydronaphthyl, 5-oxo-5,6,7,8-tetrahydronaphthyl, indenyl, 5,8-dihydronaphthyl or naphthyl radical; wherein $R^4$ stands for a radical of the formula:

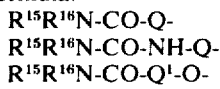
$R^{15}R^{16}N$-CO-Q-
$R^{15}R^{16}N$-CO-NH-Q-
$R^{15}R^{16}N$-CO-Q$^1$-O-
or
$R^{26}$-X-NR$^{15}$-Q- wherein Q stands for a direct link or for an alkylene or alkenylene radical each of up to 6 carbon atoms; wherein $Q^1$ stands for an alkylene radical of up to 6 carbon atoms; wherein $R^{15}$ stands for the hydrogen atom or for an alkyl radical of up to 6 carbon atoms; wherein $R^{16}$ stands for the hydrogen atom, or for an alkenyl, cycloalkyl, hydroxyalkyl or alkoxyalkyl radical each of up to 6 carbon atoms, or for an alkyl, aryl, aralkyl or aralkenyl radical each of up to 10 carbon atoms; wherein X stands for the carbonyl (-CO-) or sulphonyl (-SO$_2$-) radical and wherein Y stands for a direct link, or for an alkylene, oxyalkylene or alkyleneoxy radical each of up to 6 carbon atoms, or for the imino (-NH-) radical, or for an alkylimino, iminoalkylene, iminoalkyleneoxy or iminoalkylenecarbonyloxy radical each of up to 6 carbon atoms, or (except when $R^1$ stands for the hydrogen atom) for the oxygen atom; or an acid-addition salt thereof.

It will be observed that the alkanolamine derivative of the invention possesses an asymmetric carbon atom, namely the carbon atom of the -CHOH- group in the alkanolamine side-chain, and it can therefore exist in racemic and optically-active forms. It is to be understood that this invention encompasses the racemic form of the alkanolamine derivative and any optically-active form which possesses βadrenergic blocking activity, it being a matter of common general knowledge how a racemic compound may be resolved into optically-active forms, and how the β-adrenergic blocking activity of these forms may be determined. It is further to be understood that β-adrenergic blocking activity usually predominates in that optically-active form which has the S absolute configuration of the said -CHOH- group.

A suitable value for the alkylene radical A is, for example, the ethylene, trimethylene, tetramethylene, hexamethylene, dodecamethylene, 1-methylethylene, 2-methylethylene or 1,1-dimethylethylene radical. A is preferably the ethylene, 1-methylethylene or 1,1-dimethylethylene radical.

A suitable value for $R^1$ when it stands for an alkyl, halogenoalkyl, alkenyl or cycloalkyl radical is, for example, the methyl, ethyl, n-propyl, isopropyl, n-butyl, isobutyl, t-butyl, n-pentyl, n-octyl, trifluoromethyl, allyl, cyclopropyl, cyclopentyl or cyclohexyl radical.

A suitable value for $R^2$, $R^3$, $R^{12}$ or $R^{13}$ when it stands for a halogen atom is, for example, the fluorine, chlorine, bromine or iodine atom.

A suitable value for $R^2$, $R^3$, $R^{12}$ or $R^{13}$ when it stands for an alkyl, cycloalkyl, alkenyl, alkynyl, alkoxy, alkylthio, cycloalkoxy, alkenyloxy, alkynyloxy or alkanoyl radical is, for example, the methyl, ethyl, n-propyl, cyclopropyl, cyclopentyl, cyclohexyl, allyl, ethynyl, methoxy, isopropoxy, methylthio, cyclopentyloxy, allyloxy, propargyloxy, formyl or acetyl radical.

A suitable value for $R^2$, $R^3$, $R^{12}$ or $R^{13}$ when it stands for an aryl or aryloxy radical is, for example, the phenyl or phenoxy radical.

A suitable value for $R^2$, $R^3$, $R^{12}$ or $R^{13}$ when it stands for an aralkoxy radical is, for example, the benzyloxy radical.

A suitable value for Q or $Q^1$ when it stands for an alkylene radical is, for example, the methylene, ethylene, trimethylene, ethylidene or 1-methylethylene radical. A suitable value for Q when it stands for an alkenylene radical is, for example, the vinylene radical.

A suitable value for $R^{15}$ when it stands for an alkyl radical is, for example, the methyl radical.

A suitable value for $R^{16}$ is, for example, the hydrogen atom or the allyl, cyclopropyl, cyclopentyl, cyclohexyl, 2-hydroxyethyl, 3-hydroxypropyl, 2hydroxy-1-methylethyl, 2-hydroxy-1,1-dimethylethyl, β-methoxyethyl, methyl, ethyl, n-propyl, isopropyl, n-butyl, isobutyl, t-butyl, n-pentyl, n-hexyl, n-nonyl, penyl, p-totyl, p-chlorophenyl, benzyl or styryl radical.

A particular value for $R^4$ is, for example, the acetamido, propionamido, methanesulphonamido, carbamoylmethyl, 3-ethylureido, 3-n-butylureido, acetamidomethyl, ureidomethyl, N-methylcarbamoylmethoxy, N-β-hydroxyethylcarbamoylmethoxy, carbamoyl, methylcarbamoyl or n-hexylcarbamoyl radical. The substituent $R^4$ is preferably in the ortho-position of the benzene ring, and a preferred substituent $R^4$ is the N-methylcarbamoylmethoxy, N-β-hydroxyethylcarbamoylmethoxy or carbamoyl radical.

A suitable value for Y when it stands for an alkylene, oxyalkylene or alkyleneoxy radical is, for example, the methylene, ethylene, oxymethylene, methyleneoxy, ethyleneoxy, trimethyleneoxy, 1-methylethylideneoxy or 1-methylpropylideneoxy radical.

A suitable value for Y when it stands for an alkylimino, iminoalkylene, iminoalkyleneoxy or iminoalkylenecarbonyloxy radical is, for example, the methylimino, iminomethylene, iminomethyleneoxy or iminomethylenecarbonyloxy radical. A suitable acid-addition salt of an alkanolamine derivative of the invention is, for example, a salt derived from an inorganic acid, for example a hydrochloride, hydrobromide, phosphate or sulphate, or a salt derived from an organic acid, for example an oxalate, lactate, tartrate, acetate, salicylate, citrate, benzoate, β-naphthoate, adipate, fumarate or 1,1-methylene-bis-(2-hydroxy-3-naphthoate), or a salt derived from an acidic synthetic resin, for example a sulphonated polystyrene resin.

A preferred alkanolamine derivative of the invention is a compound of the formula given above wherein A stands for an alkylene radical of from 2 to 6 carbon atoms, especially the ethylene, 1-methylethylene or 1,1-dimethylethylene radical; wherein $R^1$ stands for the hydrogen atom or for an alkyl, alkenyl or cycloalkyl radical each of up to 6 carbon atoms, especially the hydrogen atom or the methyl, ethyl, n-propyl, isopropyl, n-butyl, t-butyl, n-pentyl, cyclopropyl or allyl radical, or $R^1$ stands for a phenyl radical of the formula:

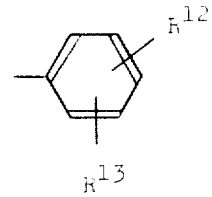

wherein $R^{12}$ and $R^{13}$, which may be the same or different, each stands for a hydrogen or halogen atom, a hydroxy, amino, nitro or cyano radical or an alkyl, alkenyl, alkoxy, alkenyloxy or alkanoyl radical each of up to 6 carbon atoms; wherein $R^2$ and $R^3$, which may be the same or different, each stands for a hydrogen or halogen atom, a nitro radical or an alkyl, alkoxy, alkylthio or cycloalkyl radical each of up to 6 carbon atoms, especially wherein $R^2$ stands for a hydrogen or halogen atom or a nitro, ethyl, methoxy or methylthio radical and $R^3$ stands for a hydrogen atom; wherein $R^4$ stands for a radical of the formula:

$R^{16}$NH-CO-Q-
$R^{16}$NH-CO-NH-Q-
$R^{16}$NH-CO-$CH_2$-O- or $R^{16}$-XNH-Q- wherein Q stands for a direct link or for the methylene radical and wherein $R^{16}$ stands for the hydrogen atom or for an alkyl or hydroxyalkyl radical each of up to 6 carbon atoms, especially the hydrogen atom or the methyl, ethyl or 2-hydroxyethyl radical; wherein X stands for the carbonyl or sulphonyl radical and wherein Y stands for a direct link or for an alkylene or alkyleneoxy radical each of up to 6 carbon atoms or for the imino radical, especially a direct link or the methylene, methyleneoxy or imino radical; or an acid-addition salt thereof.

One particularly preferred alkanolamine derivative of the invention is a compound of the formula:

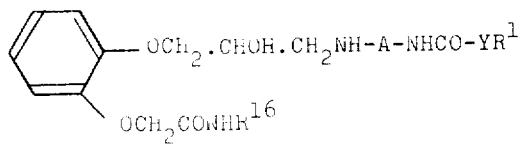

wherein A stands for the ethylene, 1-methylethylene or 1,1-dimethylethylene radical; wherein $R^1$ stands for the hydrogen atom or for an alkyl, alkenyl or cycloalkyl radical each of up to 6 carbon atoms, or for a phenyl radical of the formula:

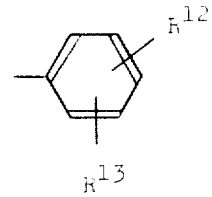

wherein $R^{12}$ and $R^{13}$, which may be the same or different, each stands for a hydrogen or halogen atom, a hydroxy, amino, nitro or cyano radical or an alkyl, alkenyl, alkoxy or alkenyloxy radical each of up to 6 carbon atoms; wherein $R^{16}$ stands for an alkyl or hydroxyalkyl radical each of up to 6 carbon atoms; and wherein Y stands for a direct link or for the methylene, methyleneoxy or imino radical; or an acid-addition salt thereof. A most particularly preferred alkanolamine of this group is such a compound wherein A and $R^{16}$ have the meanings stated above, $R^1$ stands for the hydrogen atom, or for an alkyl radical of up to 6 carbon atoms, or for an unsubstituted phenyl radical and Y stands for a direct link or for the methylene or imino radical, and especially such a compound wherein $R^{16}$ stands for the methyl or 2-hydroxyethyl radical, or an acid-addition salt thereof.

A second particularly preferred alkanolamine derivative of the invention is a compound of the formula:

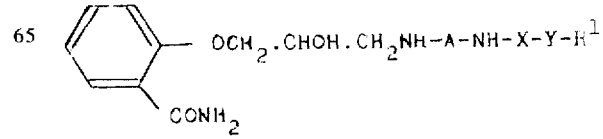

wherein A stands for the ethylene, 1-methylethylene or 1,1-dimethylethylene radical, R$^1$ stands for the hydrogen atom or for an alkyl or alkenyl radical each of up to 6 carbon atoms, or for an unsubstituted phenyl radical, X stands for the carbonyl or sulphonyl radical and Y stands for a direct link or for the methylene or imino radical, or an acid-addition salt thereof.

Specific alkanolamine derivatives of the invention are those hereinafter described in the Examples. Of these, preferred compounds by virtue of their high cardioselective β-adrenergic blocking activity (as hereinafter defined) are:

1-o-(N-β-hydroxyethylcarbamoylmethoxy)phenoxy-3-β-phenylacetamidoethylamino-2-propanol;
1-o-(N-methylcarbamoylmethoxy)phenoxy-3-β-acetamidoethylamino-2-propanol;
1-o-(N-methylcarbamoylmethoxy)phenoxy-3β-isobutyramidoethyamino2-propanol;
1-o-(N-methylcarbamoylmethoxy)phenoxy-3-β-(3-n-butylureido)-ethylamino-2-propanol;
1-o-(N-methylcarbamoylmethoxy)phenoxy-3-β-phenylacetamido-ethylamino-2-propanol;
1-o-(N-methylcarbamoylmethoxy)phenoxy-3-β-(o-allylphenoxy)-acetamidoethylamino-2-propanol;
1-o-(N-methylcarbamoylmethoxy)phenoxy-3-(1,1-dimethyl-2-isobutyramidoethyl)amino-2-propanol;
1-o-(N-β-hydroxyethylcarbamoylmethoxy)phenoxy-3-β-isobutyramidoethylamino-2-propanol;
1-o-(N-β-hydroxyethylcarbamoylmethoxy)phenoxy-3-(1-methyl-2-phenylacetamidoethyl)amino-2-propanol;
1-o-carbamoylphenoxy-3-β-(3-phenylureido)ethylamino-2-propanol;
1-o-carbamoylphenoxy-3-β-isobutyramidoethylamino-2-propanol;
1-o-carbamoylphenoxy-3-β-phenylacetamidoethylamino-2-propanol;
1-o-carbamoylphenoxy-3-β-benzenesulphonamidoethylamino-2-propanol;
1-o-carbamoylphenoxy-3-(1-methyl-2-phenylacetamidoethyl)amino-2-propanol;
1-(2-ethyl-4-propionamidophenoxy)-3-β-phenylacetamidoethylamino-2-propanol;
1-(2-ethyl-4-propionamidophenoxy)-3-β-(3-phenylureido)ethylamino-2-propanol; and
1-o-methanesulphonamidophenoxy-3-β-isobutyramidoethylamino-2-propanol;

and the acid-addition salts thereof.

The alkanolamaine derivative of the invention may be manufactured by any chemical process known to be useful for the manufacture of chemically-analogous compounds.

According to a further feature of the invention there is provided a process for the manufacture of the alkanolamine derivative of the invention which comprises assembling in sequence, by chemical synthesis, the six radicals:

i. a radical of the formula R$^4$-, wherein R$^4$ has the meaning stated above;
ii. an aryleneoxy radical of the formula:

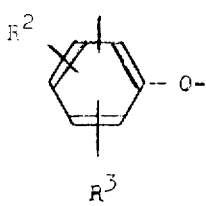

wherein R$^2$ and R$^3$ have the meanings stated above;
iii. an oxygenated three-carbon radical of the formula:

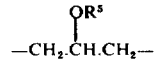

wherein R$^5$ stands for hydrogen or for the protecting group;
iv. an imino radical of the formula -NR$^6$-, wherein R$^6$ stands for hydrogen or for a protecting group;
v. a radical of the formula:

wherein A has the meaning stated above and wherein R$^7$ stands for hydrogen or for a protecting group; and
vi. a radical of the formula:

wherein R$^1$, X and Y have the meanings stated above; whereafter if one or more of R$^5$, R$^6$ and R$^7$ stands for a protecting group, the one or more protecting groups are removed.

The various stages of the assembly may be carried out in any possible order. Thus, for example:
a. a phenol of the formula:

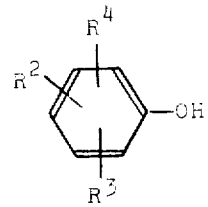

wherein R$^2$, R$^3$ and R$^4$ have the meanings stated above, may first be reacted with an oxygenated three-carbon derivatives, for example a compound of the formula:

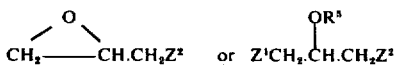

wherein R$^5$ has the meaning stated above, wherein Z$^1$ stands for a displaceable radical and wherein Z$^2$ stands for the hydroxy radical or for a displaceable radical. If Z$^2$ stands for the hydroxy radical, the intermediate compound obtained is further reacted with a reagent which will replace the primary hydroxy radical Z$^2$ with a displaceable radical Z$^1$. The resulting product, which is a compound of the formula:

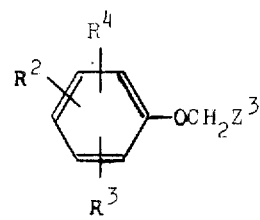

wherein $R^2$, $R^3$ and $R^4$ have the meanings stated above and wherein $Z^3$ stands for the group

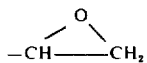

or the group

wherein $R^5$ and $Z^1$ have the meanings stated above, or which may be, when $R^5$ stands for hydrogen, a mixture of such compounds wherein $Z^3$ has both meanings stated above, is then reacted with an amine of the formula:

HNR⁶-A-NR⁷AX-Y-R¹ wherein A, $R^1$, $R^6$, $R^7$, X and Y have the meanings states above, or with a precursor of such an amine.

b. An oxygenated three-carbon derivative, for example a compound of the formula:

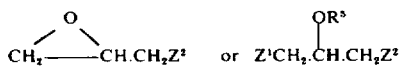

wherein $R^5$, $Z^1$ and $Z^2$ have the meanings stated above, is reacted with an amine of the formula:

HNR⁶-A-NR⁷-X-Y-R¹ wherein A, $R^1$, $R^6$, $R^7$, X and Y have the meanings stated above, or with a precursor of such an amine. If $X^2$ stands for the hydroxy radical the intermediate compound obtained is further reacted with a reagent which will replace the primary hydroxy radical $Z^2$ with a displaceable radical $Z^1$. The resulting product, which is a compound of the formula:

Z¹CH₂-NR⁶-A-NR⁷-X-Y-R¹ wherein A, $R^1$, $R^6$, $R^7$, X, Y and $Z^3$ have the meanings stated above, or which may be, when $R^5$ stands for hydrogen, a mixture of such compounds wherein $Z^3$ has both meanings stated above, is then reacted with a phenol of the formula:

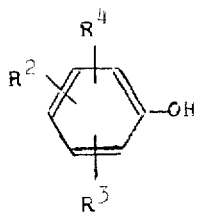

wherein $R^2$, $R^3$ and $R^4$ have the meanings stated above.
Alternatively, the compound of the formula:

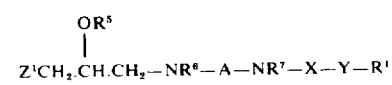

may be converted, by heating, into the azetidinol derivative of the formula:

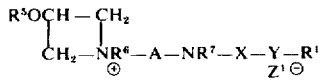

When $R^6$ stands for hydrogen, the azetidinol salt is converted into its free base form and then reacted with a phenol of the formula stated above. When $R^6$ stands for a protecting group, the azetidinium salt is reacted directly with the said phenol. The azetidinol derivative may alternatively be obtained by the reaction of a compound of the formula:

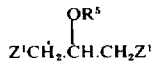

wherein $R^5$ and $Z^1$ have the meanings stated above, with an amine of the formula:

HNR⁶-A-NR⁷-X-Y-R¹ wherein A, $R^1$, $R^6$, $R^7$, X and Y have the meanings stated above.

A suitable value for $Z^1$, or for $Z^2$ when it stands for a displaceable radical, is, for example, a halogen atom, for example the chlorine or bromine atom, or a sulphonyloxy radical, for example an alkanesulphonyloxy radical of up to 6 carbon atoms or an arenesulphonyloxy radical of up to 10 carbon atoms, for example the methanesulphonyloxy, benzenesulphonyloxy or toluene-p-sulphonyloxy radical.

A suitable reagent which will replace the primary hydroxy radical $Z^2$ with a displaceable radical $Z^1$ is, for example, a halogenating agent, for example a thionyl halide, for example thionyl chloride or thionyl bromide, or a sulphonylating agent, for example an alkanesulphonyl halide or an arenesulphonyl halide, for example methanesulphonyl chloride, benzenesulphonyl chloride or toluene-p-sulphonyl chloride.

The reaction involving a phenol reactant may be carried out in the presence of an acid-binding agent, for example an alkali metal hydroxide, for example sodium hydroxide, or an organic base, for example piperidine. Alternatively, an alkali metal derivative of the phenol reactant, for example the sodium or potassium derivative, may be used as starting material. The reaction may be carried out in a diluent or solvent, for example methanol or ethanol, and it may be accelerated or completed by the application of heat, for example by heating to the boiling point of the diluent or solvent.

The reaction involving an amine of the formula:

HNR⁶-A-NR⁷-X-Y-R¹ may be carried out at ambient temperature or it may be accelerated or completed by the application of heat, for example by heating to a temperature of 90°–110°C.; it may be carried out at atmospheric or at an elevated pressure, for example by heating in a sealed vessel; and it may be carried out in an inert diluent or solvent, for example methanol, ethanol or n-propanol, or an excess of the amine may be used as diluent or solvent.

c. The series of reactions described under (a) or (b) above may be carried out except that an amine of the formula $R^6NH_2$ is used in place of an amine of the formula:

$$HNR^6\text{-}A\text{-}NR^7\text{-}X\text{-}Y\text{-}R^1$$

it being understood that when $R^6$ stands for hydrogen the amine is ammonia.

$$\text{-}A\text{-}NR^7\text{-}X\text{-}Y\text{-}R^1$$

The radical may then be inserted as a separate step, for example either by the reaction of the final product from the series of reactions described under (a) or (b) above with a compound of the formula:

$$Z^1\text{-}A\text{-}NR^7\text{-}X\text{-}Y\text{-}R^1$$

wherein A, $R^1$, $R^7$, X, Y and $Z^1$ have the meanings stated above, or, when $R^6$ stands for hydrogen, by the reaction under reducing conditions of the final product from the series of reactions described under (a) and (b) above with a carbonyl compound of the formula:

$$A^1\text{-}CO\text{-}A^1\text{-}NR^7\text{-}X\text{-}Y\text{-}R^1$$

wherein $R^1$, $R^7$, X and Y have the meanings stated above and wherein $A^1$ stands for hydrogen or for an alkyl radical and $A^2$ stands for an alkylene radical such that the radical $$\begin{array}{c} A^1 \\ | \\ -CH-A^2- \end{array}$$

has the same meaning as is stated above for A.

The reaction involving a compound of the formula:

$$Z^1\text{-}A\text{-}NR^7\text{-}X\text{-}Y\text{-}R^1$$

may conveniently be carried out in the presence of a base, for example sodium or potassium carbonate, in a diluent or solvent, for example ethanol or isopropanol, at an elevated temperature, for example at the boiling point of the diluent or solvent.

Suitable reducing conditions for the reaction involving the carbonyl compound are those provided by the presence of hydrogen and a hydrogenation catalyst, for example palladium or platinum, in an inert diluent or solvent, for example in one or more solvents selected from water, ethanol and an excess of the carbonyl compound used as starting material; or by the presence of an alkali metal borohydride, for example sodium borohydride or lithium cyanoborohydride, in an inert diluent or solvent, for example in one or more solvents selected from water, ethanol, methanol and an excess of the carbonyl compound used as starting material. It is to be understood that when in the starting material $R^1$ stands for an alkenyl radical, or one or more of $R^2$, $R^3$, $R^{12}$ and $R^{13}$ stands for a halogen atom or for a nitro, cyano, alkenyl, alkynyl, alkylthio, alkenyloxy, alkynyloxy or α-aralkoxy radical, hydrogen and a hydrogenation catalyst are preferably not used to provide the reducing conditions, in order to prevent the radical $R^1$, $R^2$, $R^3$, $R^{12}$ or $R^{13}$ from being affected by catalytic hydrogenation.

d. The series of reactions described under (a) or (b) above may be carried out except that an amine of the formula:

$$HNR^6\text{-}A\text{-}NHR^7$$

wherein $R^6$, $R^7$ and A have the meanings stated above, is used in place of an amine of the formula:

$$NHR^6\text{-}A\text{-}NR^7\text{-}X\text{-}Y\text{-}R^1$$

or the reaction described under (c) above may be carried out except that the radical $\text{-}A\text{-}NHR^7$ is inserted in place of the radical $\text{-}A\text{-}NR^7\text{-}X\text{-}Y\text{-}R^1$. The amidic linkage $\text{-}NR^7\text{-}X\text{-}$ may then be formed as a separate step by reaction of the resulting product, which is a compound of the formula:

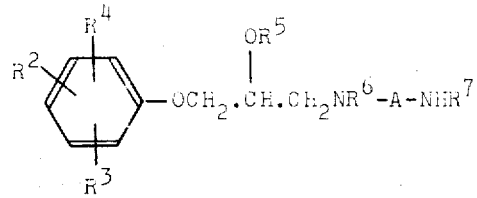

wherein $R^2$, $R^3$, $R^4$, $R^5$, $R^6$, $R^7$ and A have the meanings stated above, with a compound of the formula:

$$Z^1\text{-}X\text{-}Y\text{-}R^1$$

wherein $R^1$, X, Y and $Z^1$ have the meanings stated above, or, when X stands for the carbonyl radical and Y stands for the imino radical, with an isocyanate of the formula:

$$OCN\text{-}R^1$$

wherein $R^1$ has the meaning stated above.

e. The series of reactions described under (a), (b), (c) or (d) above may be carried out except that the substituent $R^4$ is not present in the molecule, and this substituent may be elaborated as the final (other than optional removal of protecting groups) step. The means for elaborating $R^4$ will depend upon the particular meaning of $R^4$. For example:

i. A compound wherein $R^4$ stands for a radical of the formula:

$$R^{15}R^{16}N\text{-}CO\text{-}Q\text{-}$$

or $$R^{15}R^{16}N\text{-}CO\text{-}Q^1\text{-}O\text{-}$$

wherein Q, $Q^1$, $R^{15}$ and $R^{16}$ have the meanings stated above, may be obtained by the reaction of a compound of the formula:

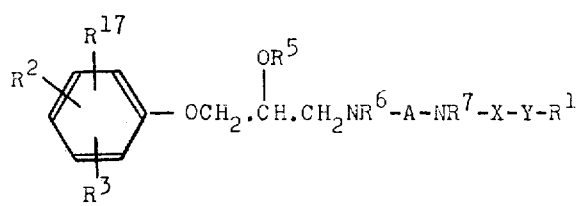

wherein A, R¹, R², R³, R⁵, R⁶, R⁷, X and Y have the meanings stated above and wherein R¹⁷ stands for a radical of the formula:

-O-COZ¹ or

-O-Q¹-COZ¹ wherein Q and Q¹ have the meanings stated above and wherein Z⁴ stands for a displaceable radical, with an amine of the formula NHR¹⁵R¹⁶, wherein R¹⁵ and R¹⁶ have the meanings stated above, whereafter if one or more of R⁵, R⁶ and R⁷ stands for a protecting group the one or more protecting groups are removed.

Z⁴ may be, for example, a halogen atom or a sulphonyloxy radical as defined above for Z¹, or it may be, for example, an alkoxy radical of up to 6 carbon atoms or an aryloxy or aralkoxy radical each of up to 10 carbon atoms, for example the phenoxy or benzyloxy radical, or it may be the hydroxy radical activated by a condensing agent such as a carbodiimide.

ii. A compound wherein R⁴ stands for a radical of the formula:

R¹⁵R¹⁶N-CO-NH-Q- wherein Q, R¹⁵ and R¹⁶ have the meanings stated above, may be obtained by the reaction of a compound of the formula:

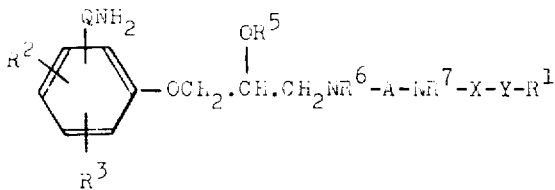

wherein A, Q, R¹, R², R³, R⁵, R⁶, R⁷, X and Y have the meanings stated above, with a compound of the formula:

R¹⁵R¹⁶NCOZ¹ wherein R¹⁵, R¹⁶ and Z¹ have the meanings stated above, or, when R¹⁵ stands for hydrogen, with an isocyanate of the formula R¹⁶NCO, wherein R¹⁶ has the meaning stated above, whereafter if one or more of R⁵, R⁶ and R⁷ stands for a protecting group the one or more protecting groups are removed.

iii. A compound wherein R⁴ stands for a radical of the formula:

R¹⁶-X-NR¹⁵-Q- wherein Q, R¹⁵ and R¹⁶ have the meanings stated above, may be obtained by the reaction of a compound of the formula:

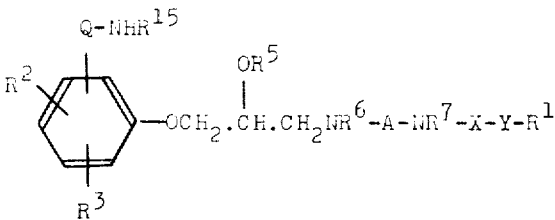

wherein A, Q, R¹, R², R³, R⁵, R⁶, R⁷, R¹⁵, X and Y have the meanings stated above, with an acylating agent of the formula R¹⁶-X-Z⁵, wherein R¹⁶ and X have the meanings stated abvove and Z⁵ stands for a displaceable radical, whereafter if one or more of R⁵, R⁶ and R⁷ stands for a protecting group, the one or more protecting groups are removed.

Z⁵ may be, for example, an halogen atom or a sulphonyloxy radical as defined above for Z¹, or it may be, for example, a radical of the formula -O-X-R¹⁶ such that the compound of the formula R¹⁶-X-Z⁵ is an acid anhydride.

iv. A compound wherein R⁴ stands for a radical of the formula:

R¹⁵R¹⁶N-CO-Q¹-O- wherein Q¹, R¹⁵ and R¹⁶ have the meanings stated above, may be obtained by the reaction of a compound of the formula:

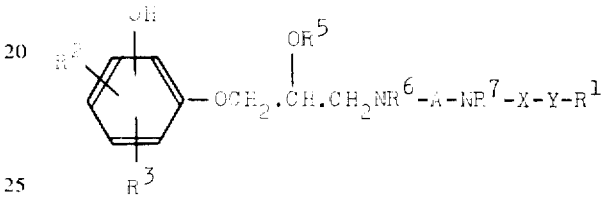

wherein A, R¹, R², R³, R⁵, R⁶, R⁷, X and Y have the meanings stated above, or a metal salt thereof, with a compound of the formula:

Z¹-O-Q¹-CONR¹⁵R¹⁶ wherein Q¹, R¹⁵, R¹⁶ and Z¹ have the meanings stated above, whereafter if one or more of R⁵, R⁶ and R⁷ stands for a protecting group, the one or more protecting groups are removed.

A suitable metal salt is, for example, the sodium salt. thallium slat.

f. A compound wherein one or more of R⁵, R⁶ and R⁷ stands for a protecting group may be prepared by the series of reactions described under (a), (b), (c), (d) or (e) above. Alternatively, a suitable protecting group may be introduced by conventional means into an intermediate compound at any stage preceding the final stage.

A suitable value for R⁵ when it stands for a protecting group is, for example, a hydrogenolysable radical, for example an α-arylalkyl, α-arylalkoxy-carbonyl or α-arylalkoxymethyl radical, for example the benzyl, benzyloxycarbonyl or benzyloxymethyl radical, or an acyl radical, for example an alkanoyl radical of up to 20 carbon atoms, for example the acetyl, t-butoxycarbonyl or 2,2,2-trichloroethoxycarbonyl radical, or an aroyl radical of up to 10 carbon atoms, for example the benzoyl radical, or an α-alkoxyalkyl radical (that is, a radical which forms with the oxygenated three-carbon radical an acetal radical), for example the tetrahydropyranyl radical, or a tertiary alkyl radical, for example the t-butyl radical.

A suitable value for R⁶ when it stands for a protecting group is, for example, a hydrogenolysable or tertiary alkyl radical as defined for R⁵, or a relatively easily hydrolysable acyl radical, for example the 2,2,2-trichloroethoxycarbonyl or t-butoxycarbonyl radical. It is to be understood that when R⁶ stands for an acyl radical, this radical must be removable under conditions which will not destroy the amidic linkage -NR⁷-X or the amidic linkage present in the substituent R⁴.

Alternatively, R⁵ and R⁶ may be joined together so that one protecting group serves to protect both the oxygen and nitrogen atoms. Such a protecting group may be for example, a radical of the formula -CHR$^8$-, wherein R$^8$ stands for hydrogen, or for an alkyl radical of up to 4 carbon atoms or an aryl radical of up to 10 carbon atoms, such that it forms, together with the adjacent oxygen and nitrogen atoms and two carbon atoms of the three-carbon radical, an oxazolidine nucleus.

A suitable value for R$^7$ when it stands for a protecting group is, for example, a hydrogenolysable or tertiary alkyl group as defined for R$^5$ or R$^6$.

The hydrogenolysable protecting group R$^5$, R$^6$ or R$^7$ may be removed, for example, by catalytic hydrogenolysis, for example by hydrogenation in the presence of a palladium-on-charcoal catalyst, in an inert diluent or solvent, for example ethanol or aqueous ethanol. The process may be accelerated or completed by the presence of an acidic catalyst, for example hydrochloric or oxalic acid.

The acyl protecting group R$^5$ or R$^6$ may be removed by hydrolysis in the presence of a base, for example an alkali metal hydroxide, in a diluent or solvent, for example water, methanol, ethanol or a mixture thereof. It is to be understood that the hydrolytic conditions used must be sufficiently mild to avoid hydrolysis of the amidic linkage -NR$^7$-X or the amidic linkage present in the substituent R$^4$.

The $\alpha$-alkoxyalkyl protecting group R$^5$ or the protecting group -R$^8$CH- formed by R$^5$ and R$^6$ taken together may be removed by hydrolysis in the presence of an acid, for example a mineral acid, for example aqueous hydrochloric acid, and the hydrolysis may be carried out at a temperature of up to 100°C.

The tertiary alkyl protecting group R$^5$, R$^6$ or R$^7$, or the acyl protecting group R$^5$ or R$^6$ when it stands for a tertiary alkoxycarbonyl radical, for example the t-butoxycarbonyl radical, may be removed by treatment with an acid, for example hydrogen chloride, in anhydrous conditions, for example in ethereal solution.

A compound wherein one or more of R$^2$, R$^3$, R$^{12}$ and R$^{13}$ stands for an $\alpha$-arylalkoxy radical, for example the benzyloxy radical, may be converted into the corresponding compound wherein one or more of R$^2$, R$^3$, R$^{12}$ and R$^{13}$ stands for the hydroxy radical by hydrogenolysis.

A preferred process for the manufacture of the alkanolamine derivative of the invention comprises the reaction of a compound of the formula:

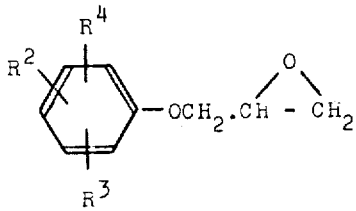

or

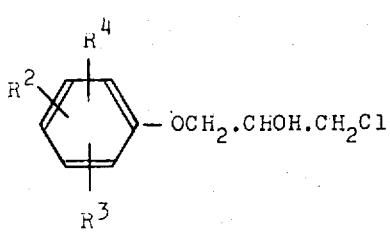

wherein R$^2$, R$^3$ and R$^4$ have the meanings stated above (both of which compounds may be obtained by the reaction of the corresponding phenol with epichlorohydrin), with an amine of the formula:

R$^6$NH-A-NH-X-Y-R$^1$ wherein A, R$^1$, X and Y have the meanings stated above and wherein R$^6$ stands for hydrogen or for the benzyl radical, whereafter if R$^6$ stands for the benzyl radical this radical is removed by hydrogenolysis.

Optionally-active enantiomorphs of the alkanolamine derivative of the invention may be obtained by the resolution by conventional means of the corresponding racemic alkanolamine derivative of the invention.

The said resolution may be carried out by reacting the racemic alkanolamine derivative with an optical-lyactive acid, followed by fractional crystallisation of the diastereoisomeric mixture of salts thus obtained from a diluent or solvent, for example ethanol, whereafter the optically-active alkanolamine derivative is liberated from the salt by treatment with a base. A suitable optically-active acid is, for example, (+)- or (−)-O,O-di-p-toluoyltartaric acid or (−)-2,3:4,5-di-O-isopropylidene-2-keto-L-gulonic acid.

The resolution process may be facilitated by treating the partially resolved alkanolamine derivative in free base form obtained after a single fractional crystallisation of the diastereoisomeric mixture of salts with a solubilising agent, for example a primary amine, for example allylamine, in a relatively non-polar diluent or solvent, for example petroleum ether.

The alkanolamine derivative of the invention in free base form may be converted into an acid-addition salt thereof by reaction with an acid by conventional means.

As stated above, the alkanolamine derivative of the invention or an acid-addition salt thereof possesses $\beta$-adrenergic blocking activity, and furthermore this acitivity is cardioselective. This activity may be determined by the reversal of isoprenaline-induced tachycardia in rats or cats, standard test for the determination of $\beta$-adrenergic blocking activity, and by relative freedom from antagonism of isoprenaline-induced vasodilation in cats or of the relief produced by isoprenaline of histamine-induced bronchospasm in guinea-pigs. Compounds exhibiting this cardioselective action show a greater degree of specificity in blocking the cardiac $\beta$-receptors than the $\beta$-receptors in peripheral blood vessels and bronchial muscle. Thus, a dose may be selected for such a compound at which the compound blocks the cardiac inotropic and chronotropic actions of a catecholamine such as isoprenaline but does not block the relaxation of tracheal smooth muscle produced by isoprenaline or the peripheral vasodilator action of isoprenaline. Because of this selective action, one of these compounds may advantageously be used together with a sympathomimetic bronchodilator, for example isoprenaline, orciprenaline, adrenaline or ephedrine, in the treatment of asthma and other obstructive airways diseases, inasmuch as the cardioselective compound will substantially inhibit the unwanted stimulatory effects of the bronchodilator on the heart but will not hinder the desirable therapeutic effect of the bronchodilator. A preferred alkanolamine derivative of the invention is three to ten times more active as a cardioselective $\beta$-adrenergic blocking agent than practolol. At doses of an alkanolamine derivative of the invention which produce effective β-adrenergic blockade in rats or cats, no symptoms of toxicity are apparent.

The alkanolamine derivative of the invention may be administered to warm-blooded animals, including man, in the form of a pharmaceutical composition comprising as active ingredient at least one alkanolamine derivative of the invention, or an acid-addition salt thereof, in association with a pharmaceutically-acceptable diluent or carrier therefor.

A suitable composition is, for example, a tablet, capsule, aqueous or oily solution or suspension, emulsion, injectable aqueous or oily solution or suspension, dispersible powder, spray or aerosol formulation.

The pharmaceutical composition may contain, in addition to the alkanolamine derivative of the invention, one or more drugs selected from sedatives, for example phenobarbitone, meprobamate, chlorpromazine and the benzodiazepine sedative drugs, for example chlordiazepoxide and diazepam; vasodilators, for example glyceryl trinitrate, pentaerythritol tetranitrate and isosorbide dinitrate; diuretics, for example chlorothiazide; hypotensive agents, for example reserpine, bethanidine and guanethidine; cardiac membrane stabilising agents, for example quinidine; agents used in the treatment of Parkinson's disease and other tremors, for example benzhexol; cardiotonic agents, for example digitalis preparations; α-adrenergic blocking agents, for example phentolamine and sympathomimetic bronchodilators, for example isoprenaline, orciprenaline, adrenaline and ephedrine.

When used for the treatment of heart diseases, for example angina pectoris and cardiac arrhythmias, or for the treatment of hypertension or anxiety states, in man, it is expected that the alkanolamine derivative would be given to man at a total oral dose of between 20 mg. and 600 mg. daily, at doses spaced at 6–8 hourly intervals, or at an intravenous dose of between 1 mg. and 20 mg.

Preferred oral dosage forms are tablets or capsules containing between 10 and 100 mg., and preferably 10 mg. or 50 mg. of active ingredient. Preferred intravenous dosage forms are sterile aqueous solutions of the alkanolamine derivative or of a non-toxic acid-addition salt thereof, containing between 0.05% and 1% w/v of active ingredient, and more particularly containing 0.1% w/v of active ingredient.

The invention is illustrated but not limited by the following Examples:

EXAMPLE 1

A mixture of 2.07 g. of 2,3-epoxy-1-(4-acetamidophenoxy)propane, 30 ml. of water, 1.68 g. of sodium hydrogen carbonate and 4.0 g of β-benzamidoethylamine hydrochloride is heated under reflux for 1 hour. The mixture is cooled and the aqueous phase is removed by decantation. The residue is crystallised from acetonitrile and there is thus obtained 1-(4-acetamidophenoxy)-3-β-benzamidoethylamino-2-propanol, m.p. 154°–156°C.

EXAMPLE 2

A mixture of 2.65 g. of 2,3-epoxy-1-(3-n-butylureido)phenoxypropane, 50 ml. of n-propanol and 1.3 g. of β-isobutyramidoethylamine is heated under reflux for 18 hours, cooled and evaporated to dryness under reduced pressure. The residue is crystallised from acetonitrile and there is thus obtained 1-p-(3-n-butylureido)phenoxy-3-β-isobutyramidoethylamino-2-propanol, m.p. 166°–168°C.

EXAMPLE 3

The process described in Example 2 is repeated except that the appropriate 2,3-epoxy-1-phenoxypropane and the appropriate β-amidoethylamine are used as starting materials. There are thus obtained the compounds described in the following table:

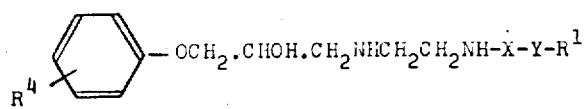

| R¹ | —X—Y— | R' | m.p. (°C.) | Crystallisation solvent |
|---|---|---|---|---|
| 4-carbamoylmethyl | —SO₂— | phenyl | 110–115 | (purified by thin-layer chromatography) |
| 2-N-methylcarbamoylmethoxy | —CO— | methyl | 127–129 | ethyl acetate/ether |
| 2-N-methylcarbamoylmethoxy | —CO— | isopropyl | 157–158 | acetonitrile |
| 2-N-methylcarbamoylmethoxy | —CONH— | n-butyl | 131–133 | ethyl acetate |
| 2-N-β-hydroxyethylcarbamoylmethoxy | —COCH₂— | phenyl | 136–138 | isopropanol |

EXAMPLE 4

The process described in Example 2 is repeated except that the appropriate 2,3-epoxy-1-phenoxypropane and the appropriate β-amidoethylamine are used as starting materials. There are thus obtained the compounds of the formula given in Example 3 which are described in the following table:

| R⁴ | —X—Y— | R¹ | m.p.(°C.) | Crystallisation solvent |
|---|---|---|---|---|
| 2-N-β-hydroxy-ethylcarbamoyl-methoxy | —CO— | isopropyl | 125–126 | acetonitrile |
| 2-N-methylcarba-molymethoxy | —CO— | t-butyl | 145–146 | ethanol |
| 2-N-methylcarba-molymethoxy | —COCH₂— | phenyl | 162–164 | methanol/acetonitrile |
| 4-acetamido | —COCH₂O— | p-acetyl-phenyl | 128–130 | ethyl acetate |
| 2-N-methylcarba-molymethoxy | —CONH— | allyl | 149–150 | acetonitrile |
| 2-N-methylcarba-molymethoxy | —CO— | cyclopropyl | 151–153 | acetonitrile |
| 2-N-methylcarba-molymethoxy | —COCH₂O— | o-allyloxy-phenyl | 122–124 | ethyl acetate |
| 2-N-methylcarba-molymethoxy | —COCH₂O— | o-allyl-phenyl | 110–111 | ethyl acetate |
| 2-N-methylcarba-molymethoxy | —COCH₂— | o-chloro-phenyl | 169–171 | acetonitrile |
| 2-N-methylcarba-molymethoxy | —COCH₂— | p-chloro-phenyl | 148–150 | acetonitrile |
| 2-N-methylcarba-molymethoxy | —COCH₂— | o-nitro-phenyl | 154–155 | acetonitrile |
| 2-N-methylcarba-molymethoxy | —COCH₂O— | o-cyano-phenyl | 134–135 | ethanol |
| 2-N-β-hydroxy-ethylcarbamoyl-methoxy | —CONH— | phenyl | 155–156 | ethanol |
| 2-carbamoyl | —CONH— | phenyl | 156–157 | ethanol |
| 2-carbamoyl | —CO— | isopropyl | 140–142 | acetonitrile |
| 2-carbamoyl | —COCH₂— | phenyl | 131–133 | ethanol |
| 2-carbamoyl | —CONH— | allyl | 140–143 | ethanol |
| 2-Carbamoyl | —SO₂— | n-propyl | 123–126 hydrogen oxalate | ethanol |
| 4-N-methyl-carbamoyl | —CO— | isopropyl | 161–162 | acetonitrile |
| 2-acetamidomethyl | —COCH₂— | phenyl | 130l 131 | acetonitrile |
| 2-N-methylcarba-molymethoxy | —COCH₂— | p-benzyloxy-phenyl | 162–164 | acetonitrile | and also the compounds described in the following table:

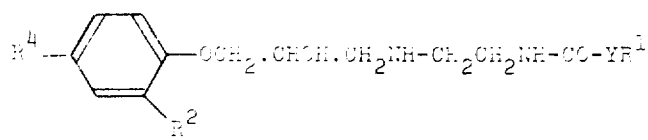

| R⁴ | R² | Y | R¹ | m.p.(°C.) | Crystallisation solvent |
|---|---|---|---|---|---|
| propionamido | ethyl | —NH— | phenyl | 168–170 | methanol/acetonitrile |
| Propionamido | ethyl | —CH₂— | Phenyl | 135–137 | acetonitrile |
| propionamido | bromo | —CH₂— | phenyl | 169–170 | ethanol |
| propionamido | methylthio | —CH₂— | phenyl | 140–142 | ethanol |
| N-hexylcarba-moyl | chloro | —NH— | phenyl | 186–188 oxalate | ethanol |
| ureidomethyl | methoxy | — | isopropyl | 151—152 | purified by thin-layer chromatography |

EXAMPLE 5

A mixture of 2.67 g. of 2,3-epoxy-1-o-(β-hydroxyethylcarbamoylmethoxy)phenoxypropane, 40 ml. of n-propanol and 1.92 g. of 2-amino-1-phenylacetamidopropane is heated under reflux for 18 hours and then evaporated to dryness under reduced pressure. The residue is dissolved in 10 ml. of ethanol and the solution is added to a solution of 1.16 g. of fumaric acid in 10 ml. of ethanol. The mixture is filtered and the solid residue is crystallised from ethanol. There is thus obtained 1-o-(β-hydroxyethylcarbamoylmethoxy)-phenoxy-3-(1-methyl-2-phenylacetamidoethyl)amino-2-propanol hemifumarate hemihydrate, m.p. 151°–153°C.

EXAMPLE 6

The process described in Example 2 is repeated except that R-(−)-2,3-epoxy-1-(2-N-methylcarbamoyl-methoxyphenoxy)propane (m.p. 74°–75°C.; $[\alpha]_D^{21}$ − 18.5°, c=2.5 in methanol; prepared from 2-N-methyl-carbamoylmethoxyphenol by a similar process to that described in the Journal of Medicinal Chemistry, 1973, 16, 168-169) and β-phenylacetamidoethylamine are used as starting materials. There is thus obtained R-(+)-1-(2-N-methylcarbamoylmethoxyphenoxy)-3-β-phenylacetamidoethylamino-2-propanol, m.p. 140°–142°C. after crystallisation from acetonitrile;

$[\alpha]_D^{21}$ + 12° (c, 1% hydrochloride in ethanol).

EXAMPLE 7

A mixture of 2.3 g. of 1-(2-carbamoylphenoxy)-3-chloro-2-propanol, 1.9 g. of 2-amino-1-phenylacetamidopropane, 40 ml. of n-propanol, 0.48 g. of sodium bicarbonate and 5 ml. of water is heated under reflux for 18 hours and then evaporated to dryness under reduced pressure. The residue is extracted twice, each time with a mixture of 25 ml. of aqueous 2N-hydrochloric acid and 25 ml. of ethyl acetate, and the aqueous acidic phases are separated, combined, basified with aqueous 11N-sodium hydroxide solution and extracted three times with 25 ml. of ethyl acetate each time. The combined ethyl acetate extracts are dried over anhydrous magnesium sulphate and evaporated to dryness under reduced pressure. The residue is chromatographed on a silica gel column (Merck 7734) using a mixture of 3 parts by volume of methanol and 7 parts by volume of chloroform as developing solvent, and the fraction which has an $R_F$ value of 0.3 when examined by thin-layer chromatography on silica gel plates using the same solvent system is collected and evaporated to dryness. There is thus obtained as residue 1-(2-carbamoylphenoxy)-3-(1-methyl-2-phenylacetamidoethyl)amino-2-propanol, the structure of which is confirmed by proton magnetic resonance spectroscopy.

The process described above is repeated except that the appropriate 2,3-epoxy-1-phenoxypropane and the appropriate amidoalkylamine are used as starting materials. There are thus obtained the compounds described in the following table:

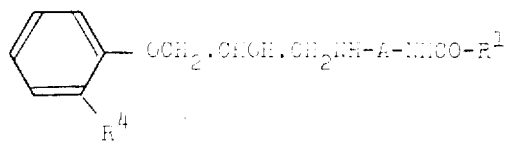

| R¹ | A | R¹ | m.p.(°C.) | Crystallisation solvent |
|---|---|---|---|---|
| N-methylcarba- | C(CH₃)₂C-H₂ - | isopropyl | (oil) | purified by chromatography |
| molymethoxy carbamoyl | -(CH₂)₆— | n-pentyl | $R_F$ 0.4 130-132 hydrogen oxalate | acetonitrile/ ethanol |

EXAMPLE 8

A mixture of 2.92 g. of 3-chloro-1-(2-nitro-4-propionamidophenoxy)-2-propanol, 1.1 g. of β-isobutyramidoethylamine and 60 ml. of n-propanol is heated under reflux for 56 hours and then evaporated to dryness under reduced pressure. 20 Ml. of aqueous 2N-hydrochloric acid are added and the mixture is extracted with 20 ml. of ether. The aqueous acidic phase is basified with aqueous 11N-sodium hydroxide solution and extracted three times with 20 ml. of ethyl acetate each time. The combined extracts are dried over anhydrous magnesium sulphate and evaporated to dryness under reduced pressure, and the residue is crystallised from acetonitrile. There is thus obtained 1-(2-nitro-4-propionamidophenoxy)-3-β-isobutyramidoethylamino-2-propanol, m.p. 140°-145°C.

The process described above is repeated except that the appropriate 3-chloro-1-phenoxy-2-propanol and the appropriate β-amidoethylamine are used as starting materials. There are thus obtained the compounds described in the following table:

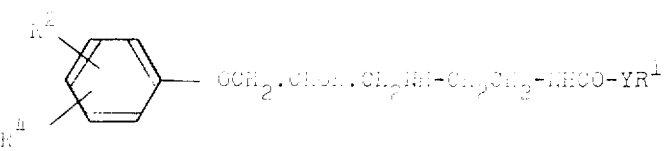

| R¹ | R² | Y | R¹ | m.p.(°C.) | Crystallisation solvent |
|---|---|---|---|---|---|
| 4-propion-amido | 2-chloro | — | isopropyl | 167-168 | ethanol |
| 4-propion-amido | 2-cyclohexyl | —CH₂— | phenyl | 169-171 hydrogen oxalate | ethanol |
| 4-acet-amidomethyl | — | — | isopropyl | 144-145 | acetonitrile |
| 4-acet-amidomethyl | — | —CH₂— | phenyl | 142-143 | isopropanol |
| 2-carbamoyl | — | —NH— | H | 167-169 hydrogen oxalate | ethanol |

EXAMPLE 9

A mixture of 2.29 g. 1-(2-carbamoylphenoxy)-3-chloro-2-propanol, 2.19 g. of N-benzyl-N-β-isobutyramidoethylamine, 0.84 g. of sodium bicarbonate, 5 ml. of water and 40 ml. of isopropanol is heated under reflux for 18 hours and then evaporated to dryness under reduced pressure. The residue is stirred with a mixture of 100 ml. of ethyl acetate and 100 ml. of water and the ethyl acetate phase is separated, dried over anhydrous magnesium sulphate and evaporated to dryness under reduced pressure. The residue is dissolved in 100 ml. of ethanol, 0.7 g. of a 30% palladium-on-charcoal catalyst is added and the mixture is shaken with hydrogen at laboratory temperature and atmospheric pressure until 210 ml. of hydrogen have been absorbed. The mixture is filtered and the filtrate is evaporated to dryness under reduced pressure. The residue is triturated once with 50 ml. of ether and then 4 times with 100 ml. of ethyl acetate each time. The mixture is filtered and the solid residue is crystallised from acetonitrile. There is thus obtained 1-(2-carbamoylphenoxy)-3-β-isobutyramidoethylamino-2-propanol, m.p. 140°–142°C.

EXAMPLE 10

A solution of 0.51 g. of acetic anhydride in 10 ml. of chloroform is added dropwise during 10 minutes to a stirred solution of 1.93 g. of 1-o-aminophenoxy-3-(N-benzyl-N-β-isobutyramidoethylamino)-2-propanol and 0.51 g. of triethylamine in 50 ml. of chloroform which is maintained at laboratory temperature, and the mixture is stirred for a further 30 minutes and then shaken successively with 50 ml. of of aqueous N-sodium hydroxide solution and 50 ml. of water. The chloroform solution is dried over anhydrous magnesium sulphate and evaporated to dryness under reduced pressure. The residue is dissolved in 50 ml. of ethanol containing 1 ml. of aqueous 11N-hydrochloric acid, 200 mg. of a 30% palladium-on-charcoal catalyst are added and the mixture is shaken with hydrogen at laboratory temperature and atmospheric pressure until 130 ml. of hydrogen have been absorbed. The mixture is filtered and the filtrate is evaporated to dryness under reduced pressure. The residue is dissolved in 20 ml. of water and the solution is neutralised with saturated aqueous sodium bicarbonate solution and extracted three times with 20 ml. of chloroform each time. The combined chloroform extracts are dried over anhydrous magnesium sulphate and evaporated to dryness. The residue is dissolved in 10 ml. of ethyl acetate and the solution is aadded to a solution of 0.6 g. of oxalic acid in 50 ml. of ethyl acetate. The mixture is filtered and the solid residue is crystallised from 25 ml. of ethanol. There is thus obtained 1-o-acetamidophenoxy-3-β-isobutyramidoethylamino-2-propanol hydrogen oxalate, m.p. 199°–200°C.

The 1-o-aminophenoxy-3-(N-benzyl-N-β-isobutyramidoethylamino)-2-propanol used as starting material may be obtained as follows:

A mixture of 19.5 g. of 2,3-epoxy-1-o-nitrophenoxypropane, 25.6 g. of N-benzyl-β-isobutyramidoethylamine hydrochloride, 4.0 g. of sodium hydroxide, 20 ml. of water and 200 ml. of n-propanol is heated under reflux for 5 hours and evaporated to dryness under reduced pressure. 200 Ml. of water are added and the mixture is extracted successively with 200 ml., 100 ml. and 100 ml. of diethyl ether. The combined ethereal extracts are dried and evaporated to dryness and the oily rsidue, which consists of 1-o-nitrophenoxy-3-(N-benzyl-N-β-isobutyramidoethylamino)-2-propanol, is used without further purification.

Raney nickel (1 g.) is added to a solution of 4.15 g. of the above compound in 50 ml. of ethanol which is heated under reflux, and a solution of 1.5 g. of hydrazine hydrate in 10 ml. of ethanol is added during 20 minutes. The mixture is heated under reflux for a further 1 hour and then cooled and filtered and the filtrate is evaporated to dryness under reduced pressure. The residue is crystallised from 30 ml. of a 2:1 v/v mixture of ethyl acetate and cyclohexane and there is thus obtained 1-o-aminophenoxy-3-(N-benzyl-N-β-isobutyramidoethylamino)-2-propanol, m.p. 94°–96°C.

EXAMPLE 11

The process described in Example 10 is repeated except that 0.36 g. of ethyl isocyanate is used in place of the 0.51 g. of acetic anhydride and that the triethylamine is omitted. There is obtained 1-o-(3-ethylureido)phenoxy-3-β-isobutyramidoethylamino-2-propanol, m.p. 162°–164°C.

EXAMPLE 12

Methanesulphonyl chloride (1.265 g.) is added to a stirred solution of 3.86 g. of 1-(2-aminophenoxy)-3-(N-benzyl-N-β-isobutyramidoethylamino)-2-propanol in 20 ml. of pyridine and the mixture iss stirred for 1½11 hours at laboratory temperature and then diluted with 200 ml. of water. The aqueous phase is removed by decantation and the resultant gum is washed with water and dissolved in a mixture of 20 ml. of aqueous N-acetic acid and 30 ml. of water. The solution is extracted three times with 50 ml. of ethyl acetate each time and the combined extracts are washed twice with 20 ml. of saturated aqueous sodium bicarbonate solution and once with 20 ml. of water, dried with anhydrous magnesium sulphate and evaporated to dryness under reduced pressure. The residue is dissolved in 40 ml. of ethanol, 200 mg. of a 30% palladium-on-charcoal catalyst are added and the mixture is shaken with hydrogen at laboratory temperature and atmospheric pressure until 140 ml. of hydrogen have been absorbed. The mixture is filtered and the filtrate is evaporated to dryness under reduced pressure. The residue is dissolved in 20 ml. of ethyl acetate and the solution is added to a solution of 1.26 g. of oxalic acid in 50 ml. of ethyl acetate. The mixture is filtered and the solid residue is crystallised from 40 ml. of ethanol. There is thus obtained 1-(2-methanesulphonamidophenoxy)-3-β-isobutyramidoethylamino-2-propanol hydrogen oxalate, m.p. 169°–171°C. (with decomposition).

EXAMPLE 13

A mixture of 1.5 g. of 1-(2-N-methylcarbamoylmethoxy)-phenoxy-3-(β-aminoethylamino-2-propanol and 1.12 g. of ethyl 3,4 -dimethoxyphenylacetate is heated at 90°C. for 18 hours. 80 Ml. of water and 20 ml. of aqueous 2N-hydrochloric acid are then added and the mixture is extracted three times with 25 ml. of chloroform each time. The combined chloroform extracts are dried over anhydrous magnesium sulphate and evaporated to dryness under reduced pressure, and the residue is crystallised from acetonitrile. There is thus obtained 3-β-(3,4-dimethoxyphenylacetamido)ethylamino-1-(2-N-methylcarbamoylmethoxyphenoxy)-2-propanol, m.p. 131°–133°C.

The 1-(2-N-methylcarbamoylmethoxyphenoxy)-3-(β-aminoethylamino)-2-propanol used as starting material may be obtained as follows:

A mixture of 1,2-epoxy-3-(2-N-methylcarbamoylmethoxyphenoxy)-2-propanol and 60 ml. of ethylene diamine is stirred at laboratory temperature for 18 hours and then evaporated to dryness under reduced pressure. The residue is dissolved in 150 ml. of water and the solution is extracted twice with 50 ml. of chloroform each time. The aqueous phase is separated and evaporated to dryness under reduced pressure. The residue consists of 1-(2-N-methylcarbamoylmethoxyphenoxy)-3-β-aminoethylamino-2-propanol, which is used without further purification.

EXAMPLE 14

A mixture of 1.37 g. of salicylamide, 30 ml. of isopropanol, 1.6 g. of sodium hydroxide, 5 ml. of water and 3.125 g. of 1-(βisobutyramidoethylamino)-3-chloro-2-propanol oxalate is heated under reflux for 18 hours. The mixture is filtered and the filtrate is evaporated to dryness under reduced pressure. The residue is dissolved in methanol and the solution is chromatographed on silica gel chromatography plates (Merck 60$F_{254}$, 2 mm. thick) using a mixture of toluene/ethyl acetate/ethanol/0.88 S.G. aqueous ammonium hydroxide solution in the ratio of 60:20:35:10 parts by volume as the developing solvent. The band having an $R_F$ value of 0.5 is removed and extracted with methanol. The methanol extract is evaporated to dryness under reduced pressure and the residue is crystallised from acetonitrile. There is thus obtained 1-(2-carbamoylphenoxy)-3-(β-isobutyramidoethylamino)-2-propanol, m.p. 139°–140°C.

EXAMPLE 15

A mixture of 1.0 g. of 1-benzymlamino-3-(2-carbamoylphenoxy)-2-propanol (prepared by conventional means from salicylamide, epichlorohydrin and benzylamine) and 0.33 g. of β-(3-phenylureido)ethyl chloride is heated at 170°C. for 5 minutes and then cooled and stirred with a mixture of 50 ml. of water and 50 ml. of ethyl acetate. The ethyl acetate phase is separated, dried over anhydrous magnesium sulphate and evaporated to dryness under reduced pressure. A mixture of 0.63 g. of the residue, which consists of 1-[N-benzyl-N-(3-phenylureido)ethylamino]-3-(2-carbamoylphenoxy)-2-propanol, 30 ml. of ethanol, 5 ml. of water and 0.1 g. of a 30% palladium-on-charcoal catalyst is shaken with hydrogen at laboratory temperature and atmospheric pressure until 110 ml. of hydrogen has been absorbed. The mixture is filtered and the filtrate is evaporated to dryness under reduced pressure. The residue is chromatographed on silica gel (merck 60$F_{254}$) chromatography plates using a 1:1 v/v mixture of methanol and dioxan as the developing solvent, and the band having an $R_F$ value of 0.3 is removed and extracted with methanol. The methanol extract is evaporated to dryness and the residue is stirred with a mixture of 10 ml. of methanol and 100 ml. of ether. The mixture is filtered and the solid residue is crystallised from ethanol. There is thus obtained 1-(2-carbamoylphenoxy)-3-[(3-phenylureido)ethylamino]-2-propanol, m.p. 150°–152°C.

EXAMPLE 16

A mixture of 1.0 g. of 3-β-(4-benzyloxyphenylacetamido)ethylamino-3-(2-N-methylcarbamoylmethoxyphenoxy)-2-propanol (Example 4), 25 ml. of ethanol and 0.1 g. of a 30% palladium-on-charcoal catalyst is shaken with hydrogen at laboratory temperature and atmospheric pressure until 130 ml. of hydrogen have been absorbed. The mixture is filtered and the filtrate is evaporated to dryness under reduced pressure. The residue is dissolved in 20 ml. of methanol and the solution is added to a hot solution of 0.3 g. of fumaric acid in a mixture of 50 ml. of ethyl acetate and 5 ml. of ethanol. The mixture is filtered and the solid residue is crystallised from methanol. There is thus obtained 3-β-(4-hydroxyphenylacetamido)ethylamino-3-(2-N-methylcarbamoylmethoxyphenoxy)2-propanol hemifumarate, m.p. 168°–170°C.

EXAMPLE 17

A mixture of 0.45 g. of 1-(2-N-methylcarbamoylmethoxyphenoxy)-3-β-(2-nitrophenylacetamido)ethylamino-2-propanol (Example 4), 0.05 g. of a 30% palladium-on-charcoal catalyst and 30 ml. of ethanol is shaken in an atmosphere of hydrogen at atmospheric pressure and at laboratory temperature until 86 ml. of hydrogen have been absorbed. The mixture is filtered, the filtrate is evaporated to dryness under reduced pressure and the residue is crystallised from ethyl acetate. There is thus obtained 3-β-(2-aminophenylacetamido)ethylamino-1-(2-N-methylcarbamoylmethoxyphenoxy)-2-propanol, m.p. 133°–135°C.

What we claim is:
1. An alkanolamine derivative selected from a compound of the formula:

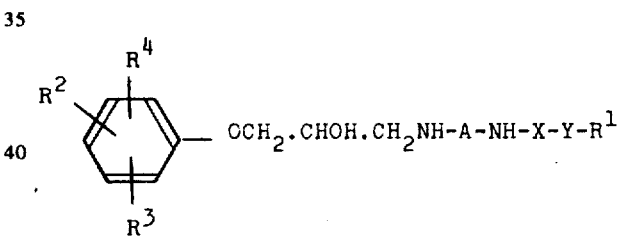

wherein A is alkylene of from 2 to 12 carbon atoms; wherein $R^1$ is hydrogen, alkyl, halogenoalkyl, alkenyl or cycloalkyl each of up to 10 carbon atoms, or aryl of the formula:

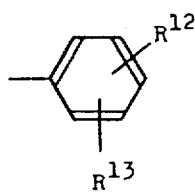

wherein $R^2$, $R^3$, $R^{12}$ and $R^{13}$, which may be the same or different, each is hydrogen, halogen, hydroxy, amino, nitro or cyano, or alkyl, cycloalkyl, alkenyl, alkynyl, alkoxy, alkylthio, cycloalkoxy, alkenyloxy, alkynyloxy or alkanoyl each of up to 6 carbon atoms, or aryl, aryloxy or aralkoxy each of up to 12 carbon atoms; or wherein $R^{12}$ and $R^{13}$ together are trimethylene, tetramethylene, propenylene, but-2-enylene or buta-1,3-dienylene such that together with the adjacent benzene ring they form respectively indanyl, 5,6,7,8-tetrahydronaphthyl, indenyl, 5,8-dihydronaphthyl or naphthyl; wherein R⁴ stands for a substituent of the formula:
R¹⁵R¹⁶N-CO-Q-
R¹⁵R¹⁶N-CO-NH-Q-
R¹⁵R¹⁶N-CO-Q¹-O-
R¹⁶-X-NR¹⁵-Q-
or wherein Q is a direct link or is alkylenne or alkenylene each of up to 6 carbon atoms; wherein Q¹ is alkylene of up to 6 carbon atoms; wherein R¹⁵ is hydrogen or alkyl of up to 6 carbon atoms; wherein R¹⁶ is hydrogen, or alkenyl, cycloalkyl, hydroxyalkyl or alkoxyalkyl each of up to 6 carbon atoms, or alkyl, aryl, aralkyl or aralkenyl each of up to 10 carbon atoms; wherein X is carbonyl (-CO-) and wherein Y is imino (-NH-), or alkylimino, iminoalkylene, iminoalkyleneoxy or iminoalkylenecarbonyloxy each of up to 6 carbon atoms, and a non-toxic, pharmaceutically-acceptable acid-addition salt thereof.

2. An alkanolamine derivative as claimed in claim 1 selected from a compound of the formula stated in claim 1 wherein A is ethylene, trimethylene, tetramethylene, hexamethylene, dodecamethylene, 1-methylethylene, 2-methylethylene or 1,1-dimethylethylene; wherein R¹ is hydrogen, methyl, ethyl, n-propyl, isopropyl, n-butyl, isobutyl, t-butyl, n-pentyl, n-octyl, trifluoromethyl, allyl, cyclopropyl, cyclopentyl or cyclohexyl or aryl of the formula:

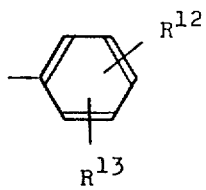

wherein R², R³, R¹² and R¹³, which may be the same or different, each is hydrogen, fluorine, chlorine, bromine, iodine, hydroxy, amino, nitro, cyano, methyl, ethyl, n-propyl, cyclopropyl, cyclopentyl, cyclohexyl, allyl, ethynyl, methoxy, isopropoxy, methylthio, cyclopentyloxy, allyloxy, propargyloxy, formyl, acetyl, phenyl, phenoxy or benzyloxy, or wherein R¹² and R¹³ together form trimethylene, tetramethylene, propenylene, but-2-enylene, or buta-1,3-dienylene; wherein R⁴ has the meaning stated in claim 1 wherein Q is a direct link or is methylene, ethylene, trimethylene, ethylidene, 1-methylethylene or vinylene, wherein Q¹ is methylene, ethylene, trimethylene, ethylidene or 1-methylethylene, wherein R¹⁵ is hydrogen or methyl and wherein R¹⁶ is hydrogen, allyl, cyclopropyl, cyclopentyl, cyclohexyl, 2-hydroxyethyl, 3-hydroxypropyl, 2-hydroxy-1-methylethyl, 2-hydroxy-1,1-dimethylethyl, β-methoxyethyl, methyl, ethyl, n-propyl, isopropyl, n-butyl, isobutyl, t-butyl, n-pentyl, n-hexyl, n-nonyl, phenyl, p-tolyl, p-chlorophenyl, benzyl or styryl; wherein X is carbonyl and wherein Y is, 1-methylpropylideneoxy, imino, methylimino, iminomethylene, iminomethyleneoxy or iminomethylenecarbonyloxy; and a non-toxic, pharmaceutically-acceptable acid-addition salt thereof.

3. An alkanolamine derivative as claimed in claim 1 which is selected from a compound of the formula:

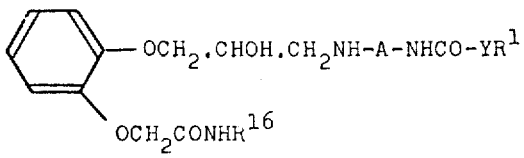

wherein A is ethylene, 1-methylethylene or 1,1-dimethylethylene; wherein R¹ is hydrogen or alkyl, alkenyl or cycloalkyl each of up to 6 carbon atoms, or aryl of the formula:

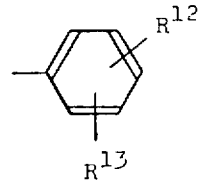

wherein R¹² and R¹³, which may be the same or different, each is hydrogen, halogen, hydroxy, amino, nitro or cyano, or alkyl, alkenyl, alkoxy or alkenyloxy each of up to 6 carbon atoms; wherein R¹⁶ is alkyl or hydroxyalkyl each of up to 6 carbon atoms; and wherein Y is imino; and a non-toxic, pharmaceutically-acceptable acid-addition salt thereof.

4. An alkanolamine derivative as claimed in claim 3 selected from a compound of the formula stated in claim 3 wherein A has the meaning stated in claim 3, R¹ is hydrogen, or alkyl of up to 6 carbon atoms, or unsubstituted phenyl, Y is imino, and R¹⁶ is methyl or 2-hydroxyethyl, and a non-toxic, pharmaceutically-acceptable acid-addition salt thereof.

5. An alkanolamine derivatives as claimed in claim 1 which is selected from a compound of the formula:

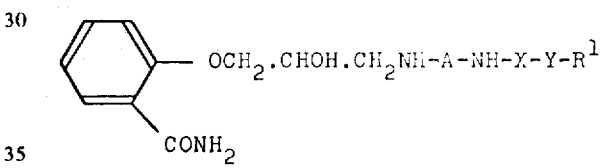

wherein A is ethylene, 1-methylethylene or 1,1-dimethylethylene, R¹ is hydrogen or alkyl or alkenyl each of up to 6 carbon atoms, or unsubstituted phenyl, X is carbonyl and Y is imino, and a non-toxic, pharmaceutically-acceptable acid-addition salt thereof.

6. An acid-addition salt as claimed in claim 1 which is a hydrochloride, hydrobromide, phosphate, sulphate, oxalate, lactate, tartrate, acetate, salicylate, citrate, benzoate, β-naphthoate, adipate, fumarate or 1,1-methylene-bis-(2-hydroxy-3-naphthoate).

7. A compound claimed in claim 1 which is selected from the group consisting of 1-o-(N-methylcarbonylmethoxy)phenoxy-3-β-(3-n-butylureido)-ethylamino-2-propanol and a non-toxic, pharmaceutically-acceptable acid-addition salt thereof.

8. A compound claimed in claim 1 which is selected from the group consisting of 1-o-carbamoylphenoxy-3-β-(3,phenylureido)ethylamino-2-propanol and a non-toxic, pharmaceutically-acceptable acid-addition salt thereof.

9. A compound claimed in claim 1 which is selected from the group consisting of 1-(2-ethyl-4-propionamidophenoxy)-3-β-(3-phenylureido)ethylamino-2-propanol.

10. An alkanolamine derivative selected from a compound of the formula:

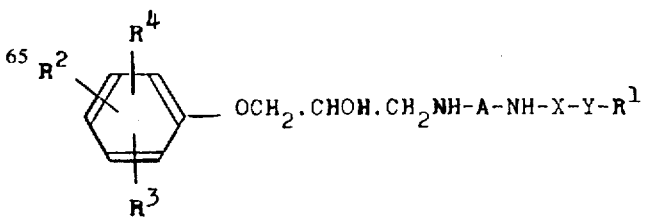

wherein A is alkylene of from 2 to 12 carbon atoms; wherein $R^1$ is hydrogen, alkyl, halogenoalkyl, alkenyl or cycloalkyl each of up to 10 carbon atoms, or aryl of the formula:

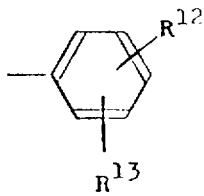

wherein $R^2$, $R^3$, $R^{12}$ and $R^{13}$, which may be the same or different, each is hydrogen, halogen, hydroxy amino, nitro or alkyl, cycloalkyl, alkenyl, alkynyl, alkoxy, alkylthio, cycloalkoxy, alkenyloxy, alkynyloxy or alkenoyl each of up to 6 carbon atoms, or aryl, aryloxy or aralkoxy each of up to 12 carbon atoms; or wherein $R^{12}$ and $R^{13}$ together are trimethylene, tetramethylene, propenylene, but-2-enylene or buta-1,3-dienylene such that together with the adjacent benzene ring they form respectively indanyl, 5,6,7,8-tetrahydronaphthyl, indenyl, 5,8-dihydronaphthyl or naphthyl; wherein $R^4$ stands for a substituent of the formula:

$R^{15}R^{16}$N-CO-Q-
$R^{15}$ $R^{16}$N-CO-NH-Q-
$R^{15}R^{16}$N-CO-$Q^1$-O-
$R^{16}$-X-N$R^{15}$-Q- or
wherein Q is a direct link or is alkylene or alkenylene each of up to 6 carbon atoms; wherein $Q^1$ is alkylene of up to 6 carbon atoms; wherein $R^{15}$ is hydrogen or alkyl of up to 6 carbon atoms; wherein $R^{16}$ is hydrogen, or alkenyl, cycloalkyl, hydroxyalkyl or alkoxyalkyl each of up to 6 carbon atoms, or alkyl, aryl, aralkyl or aralkenyl each of up to 10 carbon atoms; wherein X is carbonyl (-CO-) and wherein Y is imino (-NH-), or alkylimino, iminoalkylene, iminoalkyleneoxy or iminoalkylene-carbonyloxy each of up to 6 carbon atoms; and a non-toxic, pharmaceutically-acceptable acid-addition salt thereof.

11. An alkanolamine derivative as claimed in claim 1 selected from a compound of the formula stated in claim 1 wherein A is ethylene, trimethylene, tetramethylene, hexamethylene, dodecamethylene, 1-methylethylene, 2-methylethylene or 1,1-dimethylethylene; wherein $R^1$ is hydrogen, methyl, ethyl, n-propyl, isopropyl, n-butyl, isobutyl, t-butyl, n-pentyl, n-octyl, trifluoromethyl, allyl, cyclopropyl, cyclopentyl or cyclohexyl or aryl of the formula:

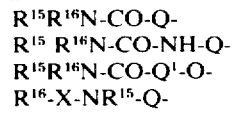

wherein $R^2$, $R^3$, $R^{12}$ and $R^{13}$, which may be the same or different, each is hydrogen, fluorine, chlorine, bromine, iodine, hydroxy, amino, nitro, methyl, ethyl, n-propyl, cyclopropyl, cyclopentyl, cyclohexyl, allyl, ethynyl, methoxy, isopropoxy, methylthio, cyclopentyloxy, allyloxy, propargyloxy, formyl, acetyl, phenyl, phenoxy or benzyloxy, or wherein $R^{12}$ and $R^{13}$ together form trimethylene, tetramethylene, propenylene, but-2-enylene or buta-1,3-dienylene; wherein $R^4$ has the meaning stated in claim 1 wherein Q is a direct link or is methylene, ethylene, trimethylene, ethylidene, 1-methylethylene or vinylene, wherein $Q^1$ is methylene, ethylene, trimethylene, ethylidene or 1-methylethylene, wherein $R^{15}$ is hydrogen or methyl and wherein $R^{16}$ is hydrogen, allyl, cyclopropyl, cyclopentyl, cyclohexyl, 2-hydroxyethyl, 3-hydroxypropyl, 2-hydroxy-1-methylethyl, 2-hydroxy-1,1-dimethylethyl, β-methoxyethyl, methyl, ethyl, n-propyl isopropyl, n-butyl isobutyl, t-butyl n-pentyl, n-hexyl, n-nonyl, phenyl, p-tolyl, p-chlorophenyl, benzyl or styryl; wherein X is carbonyl and wherein Y is imino, methylimino, iminomethylene, iminomethyleneoxy or iminomethylenecarbonyloxy; and a non-toxic, pharmaceutically-acceptable acid-addition salt thereof.

12. An alkanolamine derivative as claimed in claim 1 which is selected from a compound of the formula:

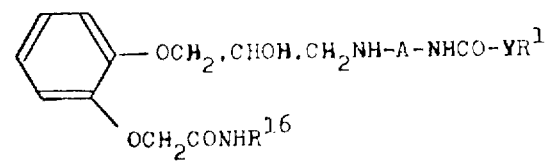

wherein A is ethylene, 1-methylethylene or 1,1-dimethylethylene; wherein $R^1$ is hydrogen or alkyl, alkenyl or cycloalkyl each of up to 6 carbon atoms, or aryl of the formula:

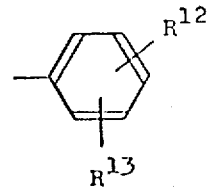

wherein $R^{12}$ and $R^{13}$, which may be the same or different, each is hydrogen, halogen, hydroxy, amino, nitro or alkyl, alkenyl, alkoxy or alkenyloxy each of up to 6 carbon atoms; wherein $R^{16}$ is alkyl or hydroxyalkyl each of up to 6 carbon atoms; and wherein Y is imino; and a non-toxic, pharmaceutically-acceptable acid-addition salt thereof.

* * * * *